United States Patent
Taraconat et al.

(10) Patent No.: US 12,259,308 B2
(45) Date of Patent: Mar. 25, 2025

(54) MEDICAL ANALYSIS DEVICE WITH IMPEDANCE SIGNAL PROCESSING

(71) Applicants: HORIBA ABX SAS, Montpellier (FR); UNIVERSITE DE MONTPELLIER, Montpellier (FR); CENTRE NATIONAL DE LA RECHERCHE SCIENTIFIQUE (CNRS), Paris (FR)

(72) Inventors: Pierre Taraconat, Montpellier (FR); Damien Isebe, Montpellier (FR); Simon Mendez, Montpellier (FR); Franck Nicoud, Montpellier (FR)

(73) Assignees: HORIBA ABX SAS, Montpellier (FR); UNIVERSITE DE MONTPELLIER, Montpellier (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 43 days.

(21) Appl. No.: 17/793,208

(22) PCT Filed: Jan. 15, 2021

(86) PCT No.: PCT/FR2021/050078
§ 371 (c)(1),
(2) Date: Jul. 15, 2022

(87) PCT Pub. No.: WO2021/144546
PCT Pub. Date: Jul. 22, 2021

(65) Prior Publication Data
US 2023/0066255 A1   Mar. 2, 2023

(30) Foreign Application Priority Data
Jan. 17, 2020 (FR) .................... 2000439

(51) Int. Cl.
*G01N 15/12* (2024.01)
*G01N 15/01* (2024.01)
*G01N 33/487* (2006.01)

(52) U.S. Cl.
CPC ....... *G01N 15/12* (2013.01); *G01N 33/48728* (2013.01); *G01N 2015/012* (2024.01)

(58) Field of Classification Search
USPC ........................................ 324/71.1
See application file for complete search history.

(56) References Cited

U.S. PATENT DOCUMENTS

| 3,919,050 A | 11/1975 | Curby |
| 5,059,395 A | 10/1991 | Brittenham et al. |

(Continued)

FOREIGN PATENT DOCUMENTS

| EP | 3396354 A1 | 10/2018 |
| FR | 1904410 | 4/2019 |

(Continued)

OTHER PUBLICATIONS

Ningquan Wang et al. "Processing code-multiplexed Coulter signals via deep convolutional neural networks" Lab on a Chip, vol. 19, No. 19, Sep. 27, 2019, pp. 3292-3304.

(Continued)

*Primary Examiner* — Vincent Q Nguyen
(74) *Attorney, Agent, or Firm* — Volpe Koenig (57) ABSTRACT

A medical analysis device with cellular impedance signal processing features a memory arranged to receive pulse data sets, with each pulse data set including impedance value data that are associated each time with a time marker. The pulse data sets together represent a curve of cellular impedance values that are measured as a cell passes through a polarised opening. The device further includes a classifier in communication with the memory. The classifier may feature a (Continued)

convolutional neural network that receives the pulse data sets as input. The classifier is provided with at least one convolutional layer, which convolutional layer has a depth greater than or equal to 3, and at least two fully connected layers, in addition to an output layer rendering a cell classification from which a pulse data set is derived.

10 Claims, 10 Drawing Sheets

(56) References Cited

U.S. PATENT DOCUMENTS

| | | | | |
|---|---|---|---|---|
| 5,805,453 | A * | 9/1998 | Sasaki | D21G 9/0009 706/900 |
| 2011/0178716 | A1* | 7/2011 | Krockenberger | G01N 33/492 702/19 |
| 2016/0273056 | A1* | 9/2016 | Scholten | C12Q 1/6895 |
| 2018/0247715 | A1 | 8/2018 | Kumar et al. | |
| 2018/0374213 | A1* | 12/2018 | Arnold | G06N 5/046 |
| 2020/0146570 | A1* | 5/2020 | Hu | A61B 5/4255 |
| 2021/0158526 | A1* | 5/2021 | Patil | G06N 3/08 |
| 2022/0196538 | A1 | 6/2022 | Taraconat et al. | |

FOREIGN PATENT DOCUMENTS

| | | |
|---|---|---|
| JP | 01-250037 A | 10/1989 |
| WO | 2019173233 A1 | 9/2019 |

OTHER PUBLICATIONS

Thomas J S Durant et al. "Very Deep Convolutional Neural Networks for Morphologic Classification of Erythrocytes" Clinical Chemistry, US, vol. 63, No. 12, Dec. 1, 2017, pp. 1847-1855.
E. A. Evans "New membrane concept applied to the analysis of fluid shear and micropipette deformed red blood cells" Biophysical Journal, 1973.
Brandao et al. "Optical tweezers for measuring red blood cell elasticity: application to the study of drug response in sickle cell disease" European Journal of Haematology, 70:207-211, 2003.
Guck et al. "The optical stretcher: a novel laser tool to micromanipulate cells" Biophysical Journal, 81:767-784, 2001.
Dobbe et al. Analyzing red blood cell-deformability distributions», Blood Cells, Molecules, and Diseases, 28:373-384, 2002.
Mohandas et al. "Analysis of factors regulating erythrocyte deformability", Journal of Clinical Investigations, 66:563-573, 1980.
Clark et al. "Osmotic gradient ektacytometry: comprehensive characterization of red cell vol. and surface maintenance", Blood, 61:899-910, 1983.
Calderon et al., "Deep Convolutional Neural Network Analysis of Flow Imaging Microscopy Data to Classify Subvisible Particles in Protein Formulations", Journal of Pharmaceutical Sciences, vol. 107, Issue 4, (2018).
Japanese Office Action mailed Oct. 1, 2024 for Japanese Patent Application No. 2022-543447.
Wang et al., "Processing code-multiplexed Coulter signals via deep convolutional neural networks" Lab on a Chip, 2019, vol. 19, p. 3292-3304.

* cited by examiner

MEDICAL ANALYSIS DEVICE WITH IMPEDANCE SIGNAL PROCESSING

FIELD OF THE INVENTION

The invention relates to the field of hematology, and in particular cellular counting and classification devices.

BACKGROUND

Since the 1950's, the counting and the volumetry of the various blood cells in hematology analyzers have been carried out by measuring impedance, according to a method known as the Coulter Principle. This method consists of passing the cells in suspension in a conductive liquid through a micro-polarized opening and of detecting the variations in electrical resistance (or variations in impedance) induced by the passages of particles through the orifice. The detection of the various pulses thus generated allows for the counting of the elements.

Different solutions have been developed in order to take account of the problems associated with circulation in an orifice (rotations due to edge or hydrodynamic effects, masking of doublets, etc.). As none of these solutions provided satisfaction, the hydrodynamic focusing technology, or hydro-focusing was developed. This solution consists of carrying out a hydrodynamic lining of the flow of cells that is to be analyzed, which makes it possible to center it in the orifice and limit the effects linked to passages at the edge. This technique is however very complex to implement and particularly expensive.

The Applicant has recently developed a solution making it possible to provide very satisfactory results while still overcoming hydro-focusing. They have protected this solution in patent application FR 1904410. During this development, the Applicant realized that their work could also be used to characterize the cells from their impedance signals, so as to return information on normality or abnormality or to characterize the morphology of these cells.

The state of the art on the existing techniques for measuring the deformability of red blood cells reveals two main families.

The first family relates to measuring techniques that are precise but long and complex to implement. For some of them, analytical models make it possible to trace back to rheological parameters such as elasticity and membrane viscosity moduli, among others. Among these methods, mention can be made of aspiration by micropipette, of which the principle is to aspirate a portion of a red blood cell in a pipette by imposing a known depression. By measuring certain quantities linked to the form of the red blood cell after aspiration, the shear modulus or the shear viscosity can be deduced (see for example the article of E. A. Evans "New membrane concept applied to the analysis of fluid shear and micropipette deformed red blood cells" Biophysical Journal, 1973). Other methods, such as the "optical tweezer" method (see for example the article of Brandao et al. "Optical tweezers for measuring red blood cell elasticity: application to the study of drug response in sickle cell disease" European Journal of Hematology, 70:207-211, 2003), or the "optical stretcher" method (see for example the article of Guck et al. "The optical stretcher: a novel laser tool to micromanipulate cells" Biophysical Journal, 81:767-784, 2001) consist of stretching the blood cell using an optical laser and of observing its shape.

The second family includes techniques making it possible to process more quickly and with greater autonomy a large number of cells and thus have a statistical idea of the deformability of the red blood cells of a sample. This type of technique studies the deformation of red blood cells using a shape parameter, called deformation index (DI), which is in fact a measurement of the stretching of the red blood cell subjected to a well-known mechanical stress. The deformation index combines the mechanical and morphological parameters of the red blood cell: it is therefore simpler to study but does not provide precise rheological information. Among these techniques, the one presented in the article of Cha et al. «Cell stretching measurement utilizing viscoelastic particle focusing" Analytical chemistry 2012 can be retained, wherein the red blood cells are stretched in the chain in an extensional flow and observed using a camera. On the same principle, but by stressing the red blood cells in a shear flow, the method described in the article of Dobbe et al. "Analyzing red blood cell-deformability distributions», Blood Cells, Molecules, and Diseases, 28:373-384, 2002, made it possible to show the impact of certain pathologies on the distributions of the deformation index of red blood cells. The article of Mohandas et al. «Analysis of factors regulating erythrocyte deformability", Journal of Clinical Investigations, 66:563-573, 1980, describes an ektacytometry wherein red blood cells are stressed in shear flow, and for which the light diffraction spectra are observed to measure the deformation index. By studying the curve of the deformation index according to the osmolarity of the suspending medium (see for example the article of Clark et al. "Osmotic gradient ektacytometry: comprehensive characterization of red cell volume and surface maintenance", Blood, 61:899-910, 1983), it was shown that certain rheological and/or morphological parameters can be measured.

Although richer in information, the methods of the first family do not make it possible to conduct a high-speed hematological analysis. Indeed, they are too long and complex to implement and require the intervention of a specialized manipulator. On the other hand, the methods of the second family, although easier to implement, remain complicated to industrialize in the framework of a medical analysis laboratory, although the study of a more global response regarding the deformation index that they offer makes it possible to isolate sub populations of red pathological blood cells.

All the methods mentioned hereinabove require an optical acquisition system or by video-microscopy. This is clearly more complicated and expensive to implement than an impedance measurement system. However, the counters operating under the Coulter Principle are not able to determine the deformation index or a simplified version of the latter.

There is therefore a need to offer a simple measuring device making it possible to discriminate cell populations according to their morphological characteristics.

SUMMARY

The invention improves the situation. To this effect, it proposes a medical analysis device with cellular impedance signal processing comprising a memory arranged to receive pulse data sets, each pulse data set comprising impedance value data that are associated each time with a time marker, these data together representing a curve of cellular impedance values that are measured when a cell passes through a polarized opening. This device further comprises a classifier comprising a convolutional neural network receiving the pulse data sets as input and is provided with at least one convolutional layer, said convolutional layer has a depth greater than or equal to 3, and at least two fully connected layers, as well as an output layer rendering a cell classification from which a pulse data set is derived.

This device is particularly advantageous because it makes it possible, with a simple measuring device, to carry out a classification of cells based on the measurement of their impedance in a Coulter Principle cytometer. In addition, it is possible to adapt the existing cytometers so as to integrate the advantages of the invention, which avoids having to purchase new devices.

According to various embodiments, the invention can have one or more of the following characteristics:
- the convolutional neural network comprises two convolutional layers, one of which is connected to the input layer that receives the pulse data sets.
- the fully connected layer comprises 4 layers of neurons,
- the activation function of all the layers of the classifier is the sigmoid function,
- the pulse data sets received in the memory are obtained from impedance measurements measured when red blood cells pass through a polarized opening,
- the output layer returns a value indicating whether a cell associated with a given pulse is normal or abnormal,
- the output layer returns a triplet indicating a morphological characteristic of a cell,
- the output layer returns a value indicating whether a cell associated with a given pulse indicates the presence of a disease such as malaria or sickle cell disease, and
- the output layer returns a value indicating information pertaining to the change over time in a sample from which a pulse data set is derived.

The invention also relates to a method for classifying a blood sample comprising the following operations:

a) receiving pulse data sets, each pulse data set comprising impedance value data that are associated each time with a time marker, these data together representing a curve of cellular impedance values that are measured when a cell passes through a polarized opening, the cells coming from the blood sample, b) for each pulse data set
  b1. determining a maximum impedance value of the pulse data set,
  b2. calculating a high impedance value by multiplying the maximum impedance value by a high coefficient chosen in the range [0.7; 0.95], and by determining in the pulse data set the time markers of which the associated impedance value in the pulse data set is equal to the high impedance value, and by calculating a high duration corresponding to the maximum duration between these time markers, and a low impedance value by multiplying the maximum impedance value by a low coefficient chosen in the range [0.1; 0.6], and by determining in the pulse data set the time markers of which the associated impedance value in the pulse data set is equal to the low impedance value, and by calculating a low duration corresponding to the maximum duration between these time markers,
  b3. calculating a peak position value equal to the division of the difference between the instant associated with the maximum impedance value and the first instant which corresponds to the low impedance value, and the low duration, and optionally a rotation value equal to the division of the high duration by the low duration, c) determining the statistical distribution of the pulse data sets according to low duration/peak position value pairs or rotation value/peak position value pairs the statistics being established with respect to a set of ranges of values of pairs, d) classifying the blood sample by comparing the distribution of the operation c) to a reference distribution of a sample of healthy blood.

BRIEF DESCRIPTION OF THE DRAWINGS

Other characteristics and advantages of the invention shall appear better when reading the description that follows, drawn from examples given for the purposes of information and in a non-limiting manner, drawn from drawings wherein:

FIG. 18 shows the statistical change over time in the measurements of FIG. 17 corresponding to Box 3' of FIG. 5.

DETAILED DESCRIPTION OF THE PREFERRED EMBODIMENTS

The drawings and the description hereinafter contain, for the most part, elements of a certain nature. They can therefore not only be used to make the present invention better understood, but also to contribute to the definition thereof, where applicable.

Figure 1:
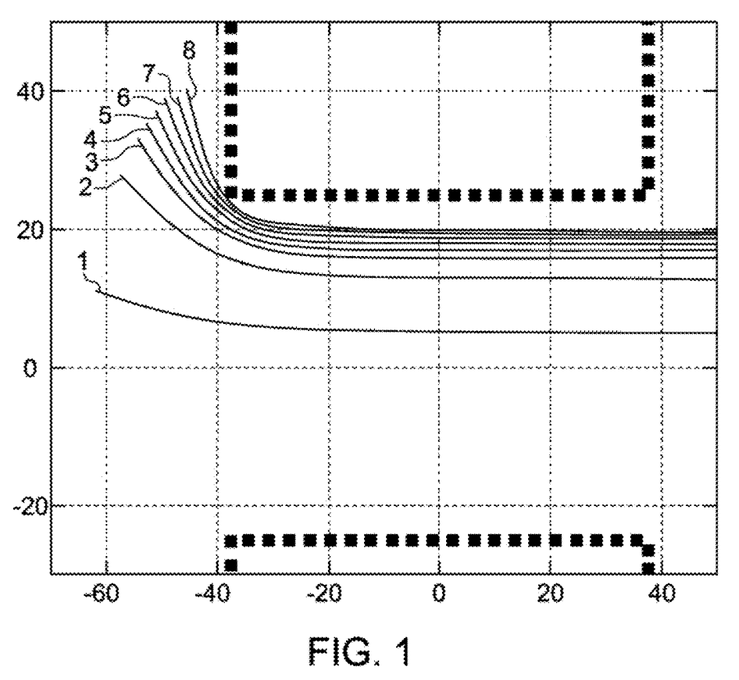
FIG. 1 shows an overview of the measuring orifice in the scope of the invention, as well as trajectories that a cell can take in the latter.

FIG. 1 shows an overview of the measuring orifice in the framework of the invention, as well as trajectories that a cell can take in the latter. The orifice has walls represented in dotted lines, the abscissa and the ordinates are expressed in μm.

Figure 2:
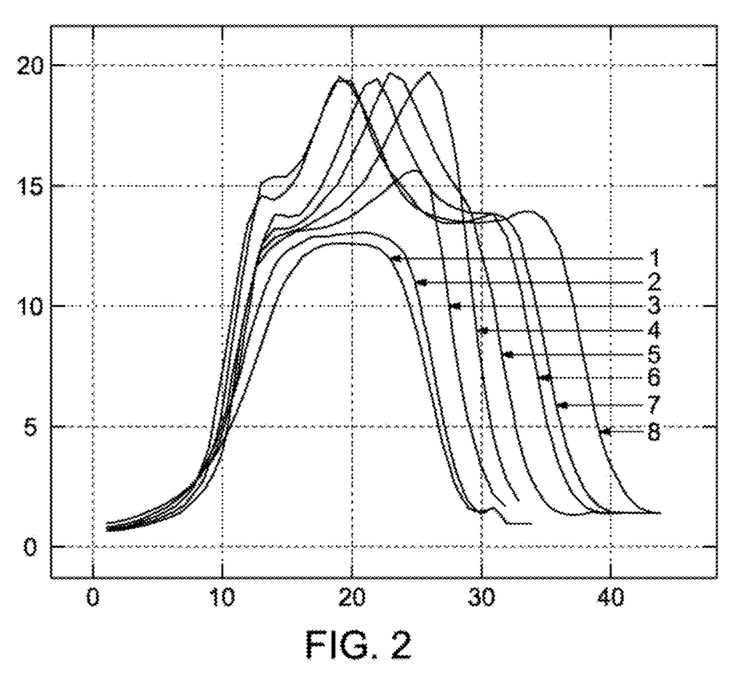
FIG. 2 shows pulse measurements for the trajectories of FIG. 1, FIG. 3 and FIG. 4 show characterization diagrams of impedance pulses of red blood cells measured with the arrangement of FIG. 1.

FIG. 2 shows the impedance pulses measured (drawn from the signal corresponding to the variation in impedance of the system due to the passing of a cell in the micro-orifice) for each one of the trajectories of FIG. 1. The abscissa are expressed in μs, while the ordinates are expressed in ohm. As can be seen, the closer the cell has an incident trajectory to one of the walls of the orifice, the more chaotic the measurement is, and the cause of errors explained in the introduction.

The works of the Applicant disclosed in application FR 1904410 have led them to develop a new magnitude to characterize impedance pulses. This magnitude is called WR, and is a ratio between two pulse widths. These widths make it possible to indicate the presence of a peak in the pulse, or on the contrary a pulse in the shape of a bell.

For this, the maximum height of the pulse in the pulse data set is first determined. The maximum height is used to calculate a high impedance value and a low impedance value.

The high impedance value is obtained by multiplying the maximum impedance value (which corresponds to the maximum height) by a high coefficient. This high coefficient is used to determine two instants which, in general, make it possible to correctly approximate the width of the impedance peak of a pulse. For this, the high coefficient is chosen in the range [0.7; 0.95], and preferably [0.8; 0.9], which ensures having at least two instants, and that these instants correspond indeed to the peak of the pulses (so as to limit the cases where several peaks are present).

Thus, the high impedance value is less than the maximum impedance value and greater than 70% of the latter. The works of the Applicant have shown that this range makes it possible to correctly capture the peaks of the pulses produced. The Applicant has identified that the value of 0.875 is particularly advantageous and gives the best results: it makes it possible to estimate the peaks of pulses as precisely as possible. Indeed, the peaks around the maximum height are in general rather narrow.

The low impedance value is obtained by multiplying the maximum impedance value by a low coefficient. This low coefficient is used to determine two instants that, in general, make it possible to correctly approximate the width of the impedance pulse. For this, the low coefficient is chosen in the range [0.1; 0.6], and preferably [0.3; 0.6] which ensures having two instants, and that these instants correspond to the general width of the pulse.

Thus, the low impedance value is comprised between 30% and 60% of the maximum impedance value. The works of the Applicant have shown that this range makes it possible to correctly capture the width of the pulses produced by eliminating the noise. The Applicant has identified that the value of 0.5 is particularly advantageous and gives the best results: the slopes of the pulses below 50% of the maximum height are very abrupt, and this value makes it possible to avoid any risk of noisy measurements.

Once the high impedance value and the low impedance value are determined, the duration between the two instants of the pulse data set which are the farthest away temporally from each other is determined, and which respectively have the high impedance value or the low impedance value. The duration associated with the high impedance value is called high duration, and the duration associated with the low impedance value is called low duration. Instinctively, it appears that the high duration corresponds substantially to the width of the impedance peak of a pulse data set, and the low duration corresponds substantially to the pulse width. Finally, the magnitude WR is determined by realizing the ratio between the high duration and the low duration.

The second magnitude is called PP and is associated with the peak of the pulse. For this, this magnitude is calculated by realizing the ratio between the difference between the instant when the pulse is maximal and the first instant that corresponds to the low impedance, and the low duration. The result is a percentage that indicates the position of the maximum pulse in the latter.

The Applicant has worked on the representations of pulses, in particular by establishing typical graphs (PP; WR). Indeed, the Applicant has discovered that this type of graph allowed them to identify interesting behaviors, in particular for the pulses characteristic of cells having been the object of a rotation.

In order to validate their hypotheses, the Applicant has altered the morphology of the red blood cells by adding specific molecules in the electrolytic solution.

Different concentrations of glutaraldehyde and N-Do-decyl-N,N-dimethyl-3-ammonio-1-propanesulfonate (also called sulfobetaine 3-12, hereinafter SB3-12), were added in the dilution reagent, then the impedances of red blood cells of a healthy blood plunged into these solutions were measured. More precisely, the preparations containing glutaraldehyde at concentrations comprised between 0% and 0.5% were prepared on the one hand, and solutions comprising SB3-12 at concentrations comprised between 0 mg/L and 90 mg/L were prepared on the other hand. The preparations were carried out separately, i.e. they each contain only an addition of or an addition of SB3-12.

It is known that the use of glutaraldehyde has a fixing effect and makes it possible to rigidify the red blood cells while still retaining their discocyte shape. Indeed, it is known that the use of SB3-12 tends to spherize the cell.

A blood sample coming from a healthy patient (for which it was verified that it did not contain any anomaly, called "healthy blood" hereinafter) was analyzed with the different concentrations in SB3-12, and another was analyzed with all the different concentrations in glutaraldehyde. Each acquisition was carried out twice, for a preliminary evaluation of the repeatability of the developments proposed.

Figure 3:
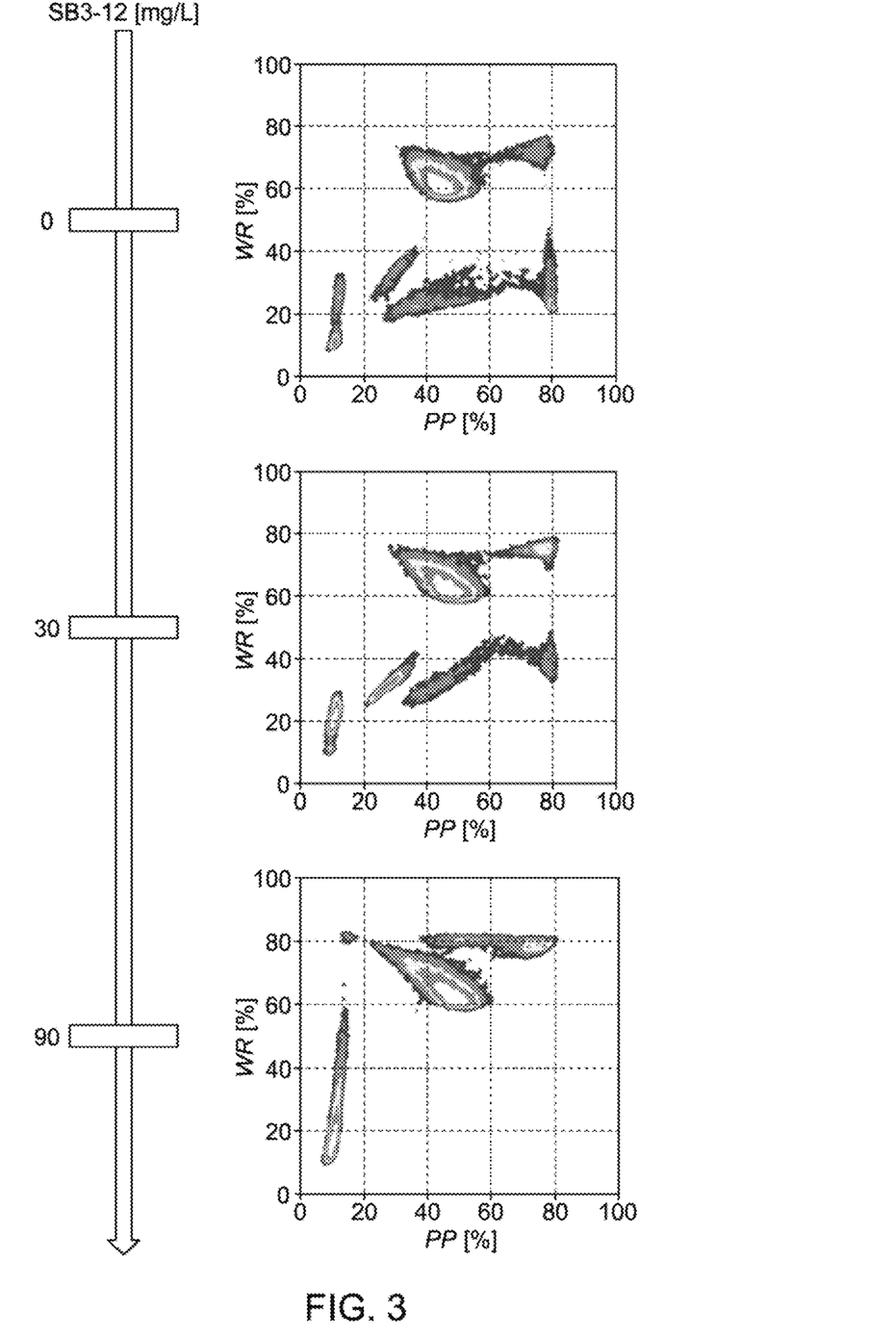
Figure 4:
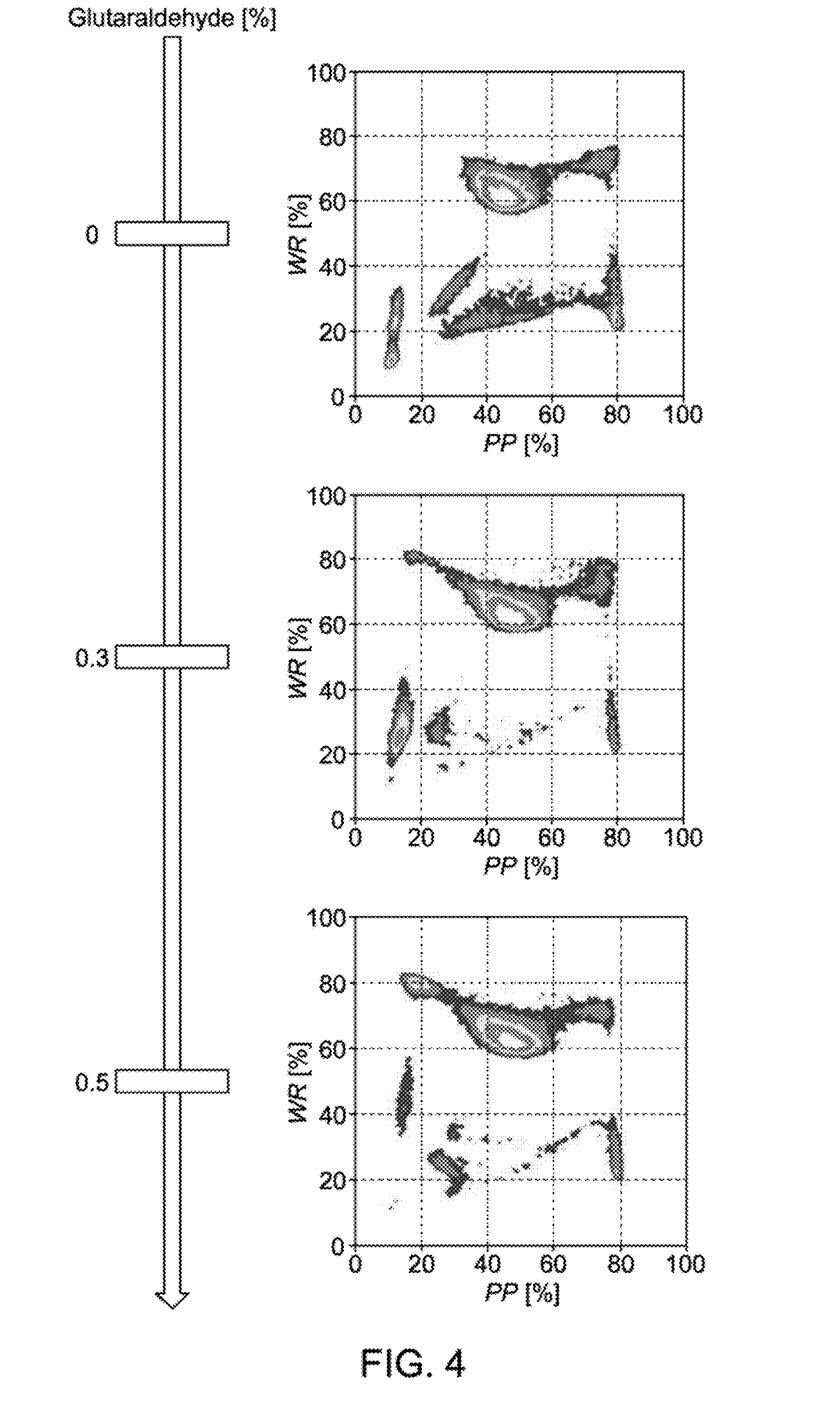

Finally, the Applicant calculated for each preparation the graph (PP; WR) of the pulses that were generated. FIG. 3 shows the graphs obtained for the preparations integrating SB3-12, while FIG. 4 shows the graphs obtained for the preparations integrating glutaraldehyde.

These graphs validated the intuitions of the Applicant, namely that they contain information on the morphological characteristics of red blood cells. Thus, the Applicant has established pulse zones (Box1' to Box6') to be studied from the graph (PP; WR) of a healthy blood, as shown FIG. 5. The pulse zones of FIG. 5 were chosen so as to highlight the differences between the acquisitions with glutaraldehyde and the acquisitions with SB3-12 (see FIG. 3 and FIG. 4).

Figure 5:
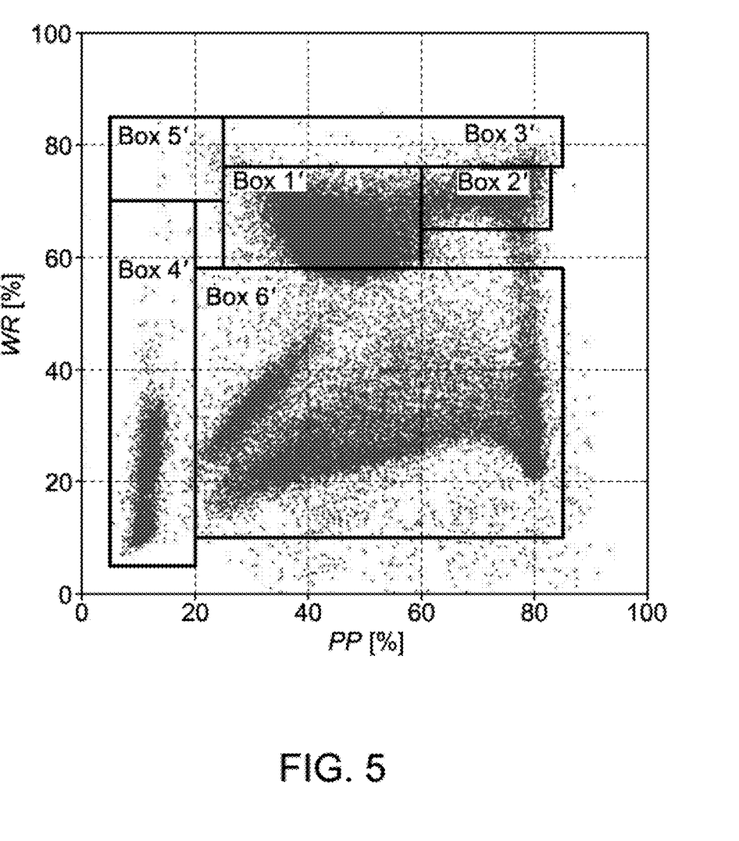
FIG. 5 shows a characterization diagram of zones of interest.

In FIG. 5, the pulse zones were defined as follows, each expressing a range PP (min; max) and WR (min; max):

Box1': (25; 60)-(58; 76)
Box2': (60; 83)-(65; 76)
Box3': (25, 85)-(76, 86)
Box4': (5, 20)-(5, 70)
Box5': (5, 25)-(70, 85)
Box6': (20, 85)-(10, 58)

In each zone of FIG. 5, the Applicant calculated the proportion of the pulses, and the averages of the magnitudes PP and WR. For a given sample, there are therefore a total of 18 parameters (3 parameters for each one of the 6 zones).

Figure 6:
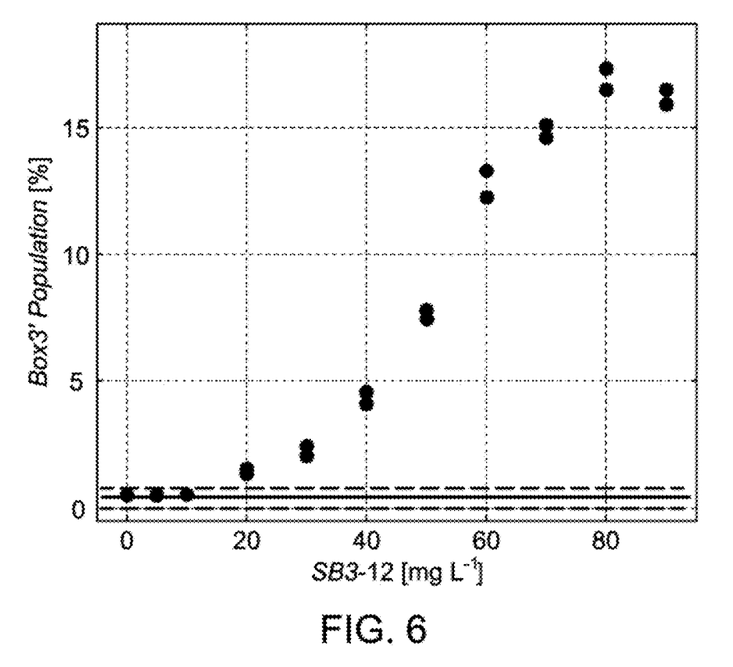
FIGS. 6 to 9 show proportions of pulses in some of the zones of interest of FIG. 5.
Figure 7:
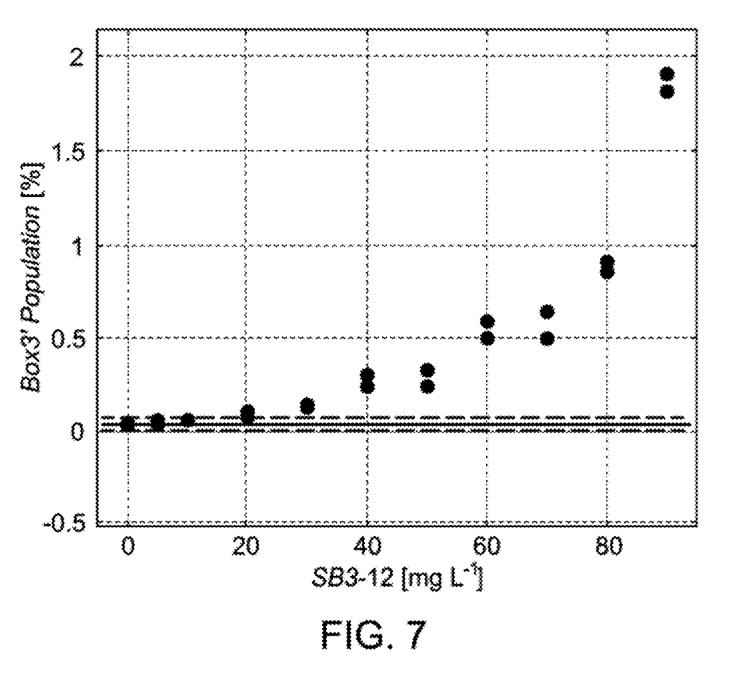
Figure 8:
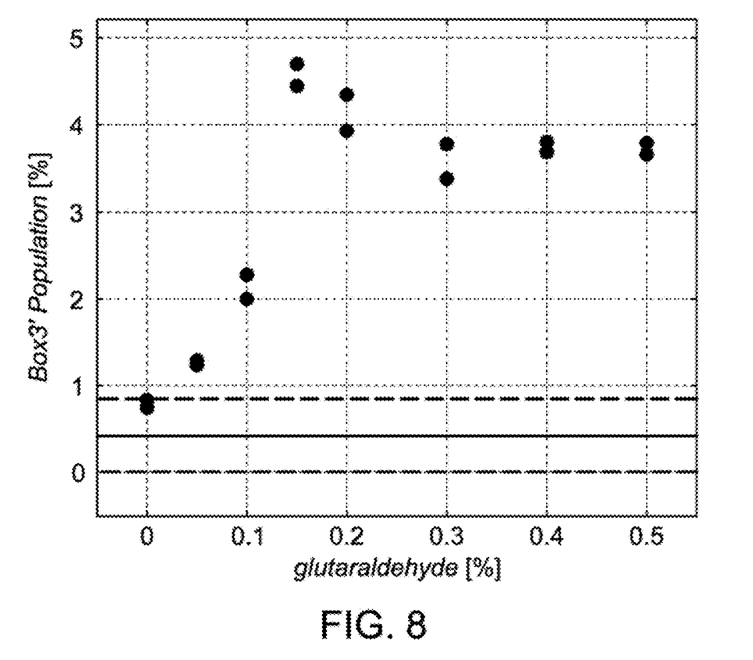
Figure 9:
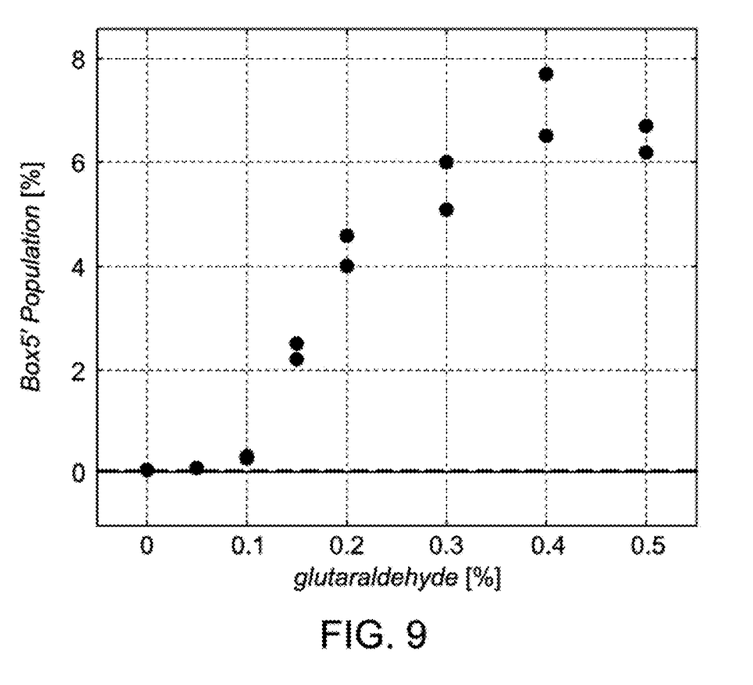

Then, the change in the proportion of pulses in the zone Box3' and the zone Box5' were shown, according to the concentration in SB3-12 (in FIGS. 6 and 7 respectively), and according to the concentration in glutaraldehyde (in FIGS. 8 and 9, respectively).

In each one of the FIGS. 6 to 9, the normality is represented by horizontal lines. The margin of error is represented by the dotted lines, and is defined as being equal to twice the standard deviation. The continuous line between the dotted lines represents the average evaluated over 22 healthy bloods defining the normality.

The analysis of FIGS. 6 to 9 reveals that when the concentration in SB3-12 or in glutaraldehyde is increased, the calculated parameters are outside the normality. These figures clearly show the influence of SB3-12 and of glutaraldehyde on red blood cells, and how they visibly change the morphological characteristics of the latter in the pulses.

By making the hypothesis that the concentration in glutaraldehyde and the concentration in SB3-12 are respectively correlated to the rigidity and the sphericity of the red blood cells, it seems possible to measure these parameters. In fact, by combining the proportion parameters of the pulses and the averages of the magnitude PP for the zone 3' on a graph, it becomes possible to quantitatively distinguish between the red blood cells having been mixed with a preparation of glutaraldehyde from those having been mixed with a preparation of SB3-12.

All these elements have made it possible to empirically validate the fact that the impedance pulses contain information relating to the morphological characteristics of red blood cells, but it does not seem that a simple function making it possible to measure the normality of red blood cells exists, or to precisely characterize their morphological abnormality where applicable.

The Applicant therefore had the idea to develop a device using a first trained neural network and configured to indicate the normality or the abnormality of a cell based on its impedance pulse, and a device using a second trained neural network and configured to classify a cell by indicating whether it has normal morphological characteristics, rigid cell morphological characteristics, or spherized cell morphological characteristics.

Figure 10:
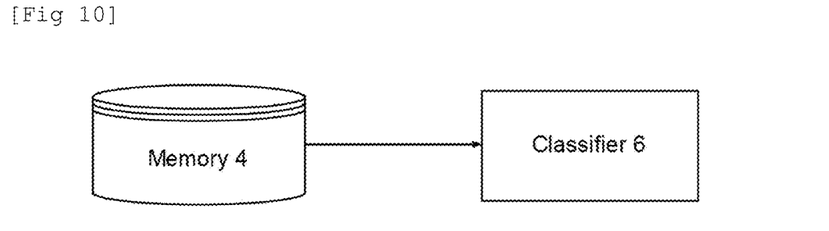
FIG. 10 shows a diagram of an embodiment of a device according to the invention.

FIG. 10 shows a generic diagram of this device. The device comprises a memory 4, and a classifier 6.

The memory 4 can be any type of data storage able to receive numerical data: hard drive, flash memory hard drive (SSD), flash memory in any form, random access memory, magnetic disc, locally distributed storage or in the cloud, etc. The data calculated by the device can be stored on any type of memory similar to the memory 4, or on the latter. This data can be erased after the device has carried out its tasks or retained.

In the example described here, the memory 4 receives pulse data sets. A pulse data set represents all the data that makes it possible to characterize an impedance pulse shown in FIG. 2. This is therefore a set of pairs (measured value of impedance; time marker), that together define a curve such as those of FIG. 2. In practice, the pulse data set will in general be a sampling of the output detection of the orifice. The pulse data set can also be a continuous curve, in which case the calculator 6 will consequently be adapted.

The classifier 6 is an element directly or indirectly accessing the memory 4. It can be carried out in the form of a suitable computer code executed on one or more processors. The term "processors" means any processor adapted to the calculations described hereinbelow. Such a processor can be carried out in any known way, in the form of a microprocessor for personal computer, a dedicated chip of the FPGA or SoC ("system on chip") type, a calculation resource on a grid or in the cloud, a microcontroller, or any other form able to provide the computational power required for the realization described hereinbelow. One or more of these elements can also be carried out in the form of specialized electronic circuits such as an ASIC. A combination of processor and of electronic circuits can also be considered.

It should be noted that the device according to the invention can advantageously be integrated into a hematological analysis device, or be offset. It can therefore be entirely integrated into the hematological analysis device or for example be a Web service to which the hematological analysis device connects when necessary or desired.

As suggested hereinabove, the classifier 6 is a neural network. Indeed, the pulses can be assimilated to images, and, with adapted training, the Applicant has considered that a neural network could be particularly effective in classifying the pulses into a set of pulse data sets with a rotation or without rotation.

Figure 11:
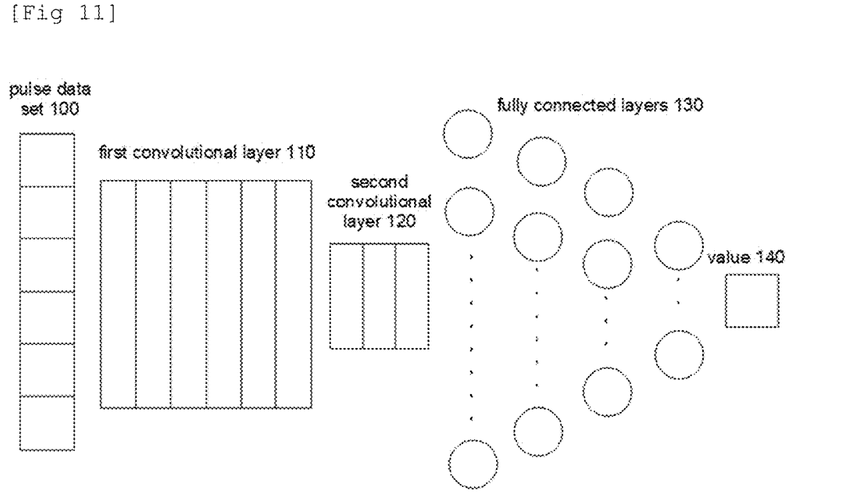
FIG. 11 shows a diagram of a neural network implemented in the embodiment of FIG. 10.
Figure 12:
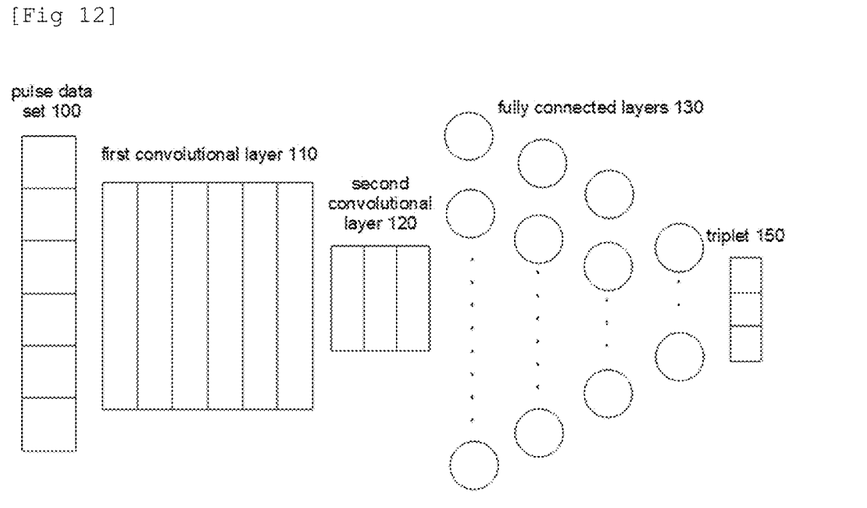
FIG. 12 shows a diagram of a neural network implemented in another embodiment of the invention.

More particularly, the Applicant has identified that a convolutional neural network was the best adapted. Thus, the architecture of the first neural network is shown in FIG. 11, while that of the second neural network is shown in FIG. 12.

In both cases, the neural network is a convolutional neural network that comprises two convolutional layers. Thus, a pulse data set 100 (comprised of 50 variables) is processed by a first convolutional layer 110 that extracts 6 characteristics, then a second convolutional layer 120 extracts 3 characteristics from the layer 110.

The filters (or convolution kernels) of the first convolutional layer 110 have a size of 8, those of the second convolutional layer 120 have a size of 3.

The convolutional layer 120 is connected to a fully connected layer 130 of the neural network which comprises a chaining of 4 layers of neurons comprising respectively 80, 40, 20 and finally 10 neurons.

In the case of the first neural network, the fully connected layer 130 returns a value 140 in the output layer. In the example described here, the value 140 is 1 if the cell is normal and 0 if it is abnormal.

For all the neurons composing the various layers of the model, the activation function retained is the sigmoid function.

For this first neural network, the training was carried out using data from acquisitions of healthy blood defining the normality, acquisitions with concentrations in SB3-12 comprised between 50 mg/L and 90 mg/L, and acquisitions with concentrations in glutaraldehyde comprised between 0.3% and 0.5%. The neural network was therefore trained to detect highly impacted cells. Each time, the training pulses had been labelled with the value 1 if the associated cell was normal and with the value 0 if the associated cell was abnormal.

The verification of the relevancy of the training was carried out by taking certain data out of the training and by introducing it into the trained neural network. The results were excellent, and, with a threshold at 0.5 on the output layer (i.e. the value 1 is returned if the output layer returns a value greater than 0.5 and 0 otherwise), the rate of false positives was 4.3% and the rate of false negatives 3.1% on the validation pulse set.

In the case of the second neural network, the fully connected layer 130 returns a triplet 150 in the output layer. In the example described here, the three components of the triplet have for value 0 or 1.

For this second neural network, the training is carried out in a manner similar to the first neural network, with the exception that the training pulses are labelled with triplets indicating whether a given pulse is normal ([1; 0; 0]), with spherization morphological characteristics ([0; 1; 0]) or with rigidification morphological characteristics ([0; 0; 1]).

The verification of the relevancy of the training was carried out by taking certain data out of the training and by introducing it into the trained neural network. The results were excellent, each element on the output layer being reduced to its maximum component, i.e. [0.92; 0.02; 0.06] returns the triplet [1; 0; 0], [0.01; 0.99; 0] returns the triplet [0; 1; 0], and [0.05; 0.25; 0.7] returns the triplet [0; 0; 1]. In these conditions, on the validation pulse set, the rate of false positives was 4% on cells classified as normal, 7.5% on cells classified with spherization morphological characteristics, and 8.2% on cells classified with rigidification morphological characteristics.

These results are excellent and demonstrate the relevancy of the device according to the invention, which makes it possible to obtain results with extreme precision with simple measurements of impedance without hydro-focusing.

The works of the Applicant have allowed them to establish that a unique convolutional layer could be sufficient, as well as a fully connected layer that would contain only 2 layers or less.

Alternatively, the Applicant considers that it is possible to use a multilayer perceptron (MLP) in place of the convolutional neural network described hereinabove. Indeed, although this type of neural network provides results that are not as precise with an equivalent number of parameters (typically, 5 to 8% additional false positives), it however constitutes a plausible alternative.

These results have opened the door to detecting pathologies that have the consequence of modifying morphological characteristics of red blood cells or of other cells, such as malaria or sickle cell disease. Each time, it is sufficient to test healthy bloods and diseased bloods in order to label the corresponding pulses, and to train the neural network of FIG. 11 or 12 with this data.

For example, by analyzing a culture sample wherein all the red blood cells are parasitized by malaria, a series of signatures labelled with this pathology is obtained and makes it possible to generate a classifier that is specific to this infection.

The Applicant has also identified that the pairing of the low duration with the magnitude PP or the magnitude WR with the magnitude PP makes it possible to make a simple distinction between normal cells and abnormal cells on a statistical basis. This makes it possible for example to implement the invention without using a neural network described hereinbelow.

Figure 13:
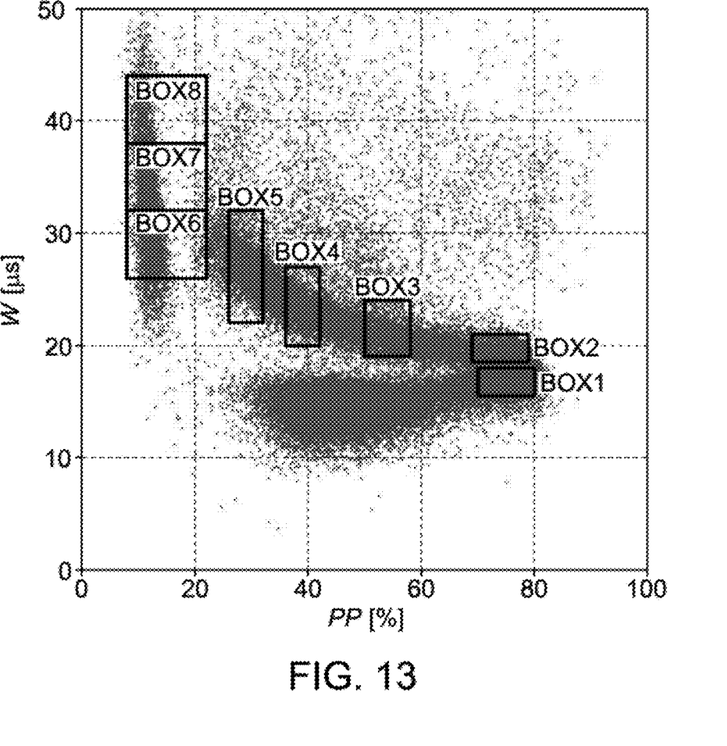
FIG. 13 shows a characterization diagram of the zones of interest.

Thus, based on a set of measurements on healthy blood, the Applicant established FIG. 13. In this figure, the Applicant has grouped together all the magnitudes drawn from pulses, which allowed them to define the pulse zones Box1 to Box8.

In FIG. 13, the pulse zones were defined as follows, each pair expressing a range PP (min; max) and WR (min; max):
Box1: (70; 80)-(15.5; 18)
Box2: (69; 79)-(18.5; 21)
Box3: (50, 58)-(19, 24)
Box4: (36, 42)-(20, 27)
Box5: (26, 32)-(22, 32)
Box6: (8, 22)-(26, 32)
Box7: (8; 22)-(32; 38)
Box8: (8; 22)-(38; 44)

Then, the Applicant repeated the same operation with the pulse data sets shown in FIG. 3 and FIG. 4 and establish two criteria for normality by comparing the population statistics for each pulse zone, for healthy blood on the one hand and for the bloods of FIGS. 3 and 4 on the other hand. Indeed, comparing population statistics makes it possible to establish significant differences for each pulse zone.

Figure 14:
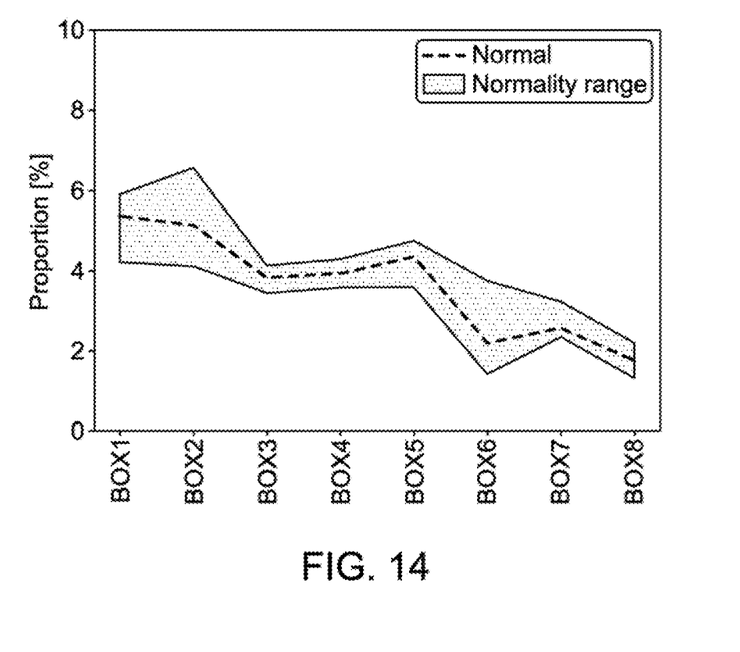
FIGS. 14 to 16 show representations of statistics of populations of pulses in some of the zones of interest of FIG. 13.

Thus, in FIG. 14, the Applicant has shown on the one hand the statistical distributions of the populations for each pulse zone for a healthy blood (as solid lines, defining a zone with a solid color), and on the other hand the value of a healthy blood as dashed lines.

Figure 15:
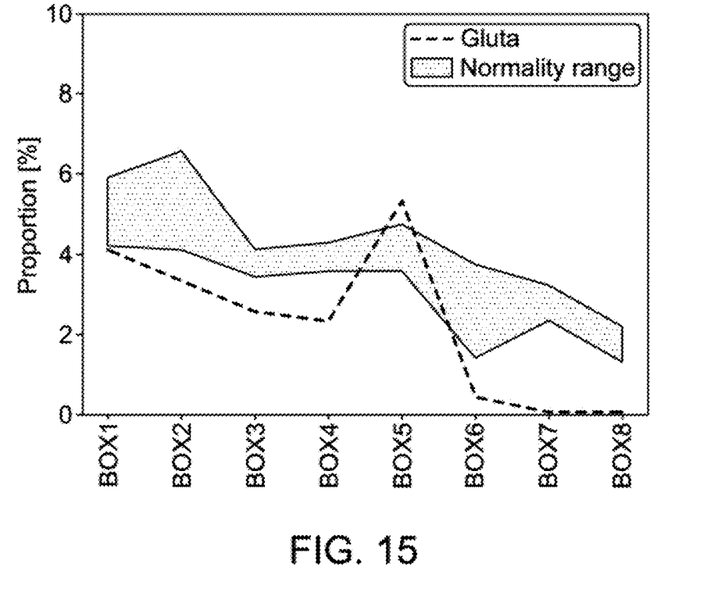

In FIG. 15 (respectively FIG. 16), the Applicant reproduced on the one hand the statistical distributions of the populations for each pulse zone for a healthy blood (as solid lines, defining a zone with a solid color, identical to those of FIG. 14), and on the other hand as dashed lines these same distributions but for pulses obtained on a blood comprising glutaraldehyde (respectively SB3-12).

Figure 16:
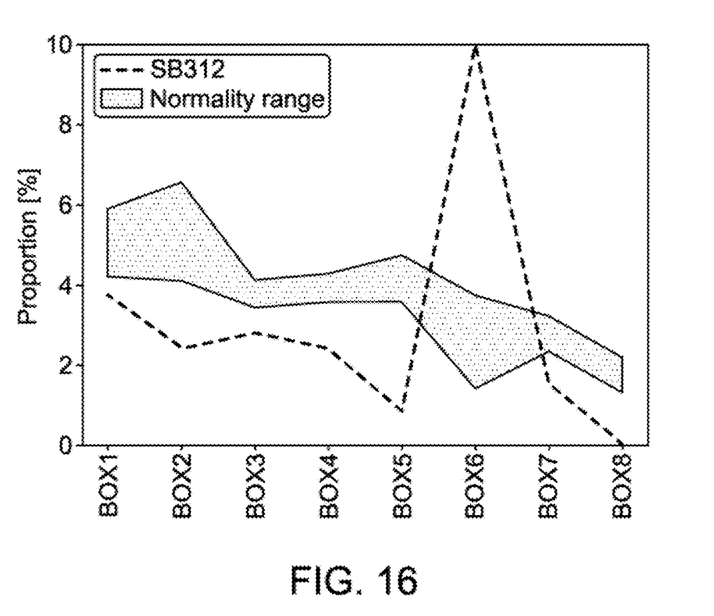

FIGS. 14 to 16 clearly show that it is sufficient to compile the population statistics for the pulses drawn from a blood sample and to compare them with the normality envelope defined by FIG. 14 (and reproduced in FIGS. 15 and 16) to determine if sample is healthy or has propensities to spherization or rigidification.

Thus, by analyzing a sufficient portion of a sample (for example about 10,000 cells, the volume of the blood analyzed being dependent on the counting conditions), it is possible to quickly return information of the "healthy blood sample" or "abnormal blood sample" type, without using a neural network.

Alternatively, instead of the graph (low duration; PP), the graph (WR; PP) could be used to establish the pulse zones making it possible to define the criteria of normality.

Figure 17:
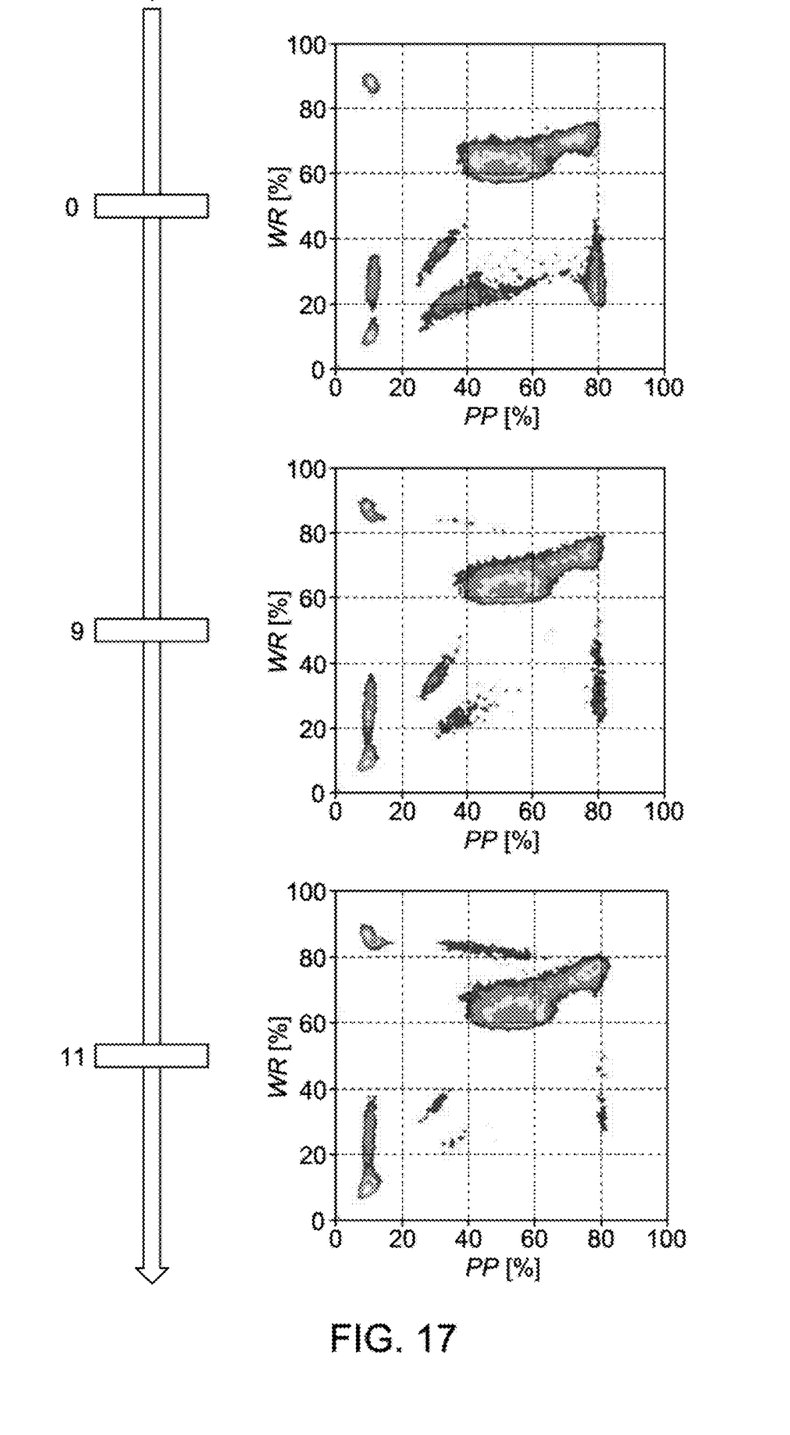
FIG. 17 shows the analysis of two healthy blood samples over a duration of 11 days.

FIG. 17 shows the analysis of two healthy blood samples over a duration of 11 days (passing as duplicate for each analysis). This figure shows that the distribution of the pulse data sets on a graph WR/PP changes according to the age of the sample.

For each analysis, the statistical distribution of the pulse data sets according to the WPP and WR/PP pairs is calculated, the statistics being established with respect to a range set of the metrics shown in FIGS. 5 and 13.

In FIG. 18, only the results pertaining to BOX3' are presented with a concern for concision. This figure shows the statistical change over time in the pulses associated with the BOX3' of FIG. 5, according to the age of the sample, the temporal origin being the day the sample was taken from the patient.

This figure shows that the blood samples remain "normal" (do not change) for 7 days, then become "abnormal", in the sense that the statistical marker starts to deviate substantially.

The invention can therefore be used to carry out a monitoring of the change over time in a blood sample. This figure is compliant with the scientific publications in the field: when the sample ages, the red blood cells present in the sample see their biomechanical characteristics degrade. In particular, it is known that the red blood cells have a decrease in elasticity over time. The change over time in a sample can be affected by the storage duration, the storage conditions, etc. In any case, FIGS. 17 and 18 shows that the arrangement according to the invention makes it possible to draw information pertaining to the change over time in the sample, indicative for example of the validity of this sample.

Although the above mainly refers to the study of red blood cells, the invention would apply to any other type of cells of which the morphological characteristics are able to change, such as platelets for example.

The invention claimed is:

1. A medical analysis device with cellular impedance signal processing comprising:
   a memory arranged to receive pulse data sets, each pulse data set comprising impedance value data that are associated each time with a time marker, each pulse data set representing a curve of cellular impedance values that are measured when a cell passes through a polarized opening, the device further comprising:
   a classifier, the classifier being an element directly or indirectly accessing the memory and comprising a convolutional neural network receiving the pulse data sets as input, the convolutional neural network comprising:
- at least one convolutional layer having a depth greater than or equal to 3,
- at least two fully connected layers, and
- an output layer rendering a classification of a cell from which one of the pulse data sets received as input is derived.

2. The device according to claim 1, wherein the convolutional neural network comprises two convolutional layers, one of which is connected to an input layer receiving the pulse data sets.

3. The device according to claim 1, wherein the fully connected layer comprises 4 layers of neurons.

4. The device according to claim 1, wherein the activation function of all the layers of the classifier is the sigmoid function.

5. The device according to claim 1, wherein the pulse data sets received in the memory are obtained from impedance measurements measured when red blood cells pass through the polarized opening.

6. The device according to claim 1, wherein the output layer returns a value indicating whether a cell associated with a given pulse is normal or abnormal.

7. The device according to claim 1, wherein the output layer returns a triplet indicating a morphological characteristic of a cell.

8. The device according to claim 1, wherein the output layer returns a value indicating whether a cell associated with a given pulse indicates the presence of a disease.

9. The device according to claim 1, wherein the output layer returns a value indicating information pertaining to the change over time in a sample from which a pulse data set is derived.

10. A method for classifying a blood sample of the medical analysis device with cellular impedance signal processing according to claim 1, comprising:

receiving pulse data sets, each pulse data set comprising impedance value data that are associated each time with a time marker, each pulse data set representing a curve of cellular impedance values that are measured when a cell passes through a polarized opening, the cells coming from the blood sample, for each pulse data set:

determining a maximum impedance value of the pulse data set, calculating a high impedance value by multiplying the maximum impedance value by a high coefficient chosen in the range of 0.7 to 0.95 and by determining in the pulse data set the time markers of which the associated impedance value in the pulse data set is equal to the high impedance value, and by calculating a high duration corresponding to the maximum duration between these time markers, and a low impedance value by multiplying the maximum impedance value by a low coefficient chosen in the range, of 0.1 to 0.6 and by determining in the pulse data set the time markers of which the associated impedance value in the pulse data set is equal to the low impedance value, and by calculating a low duration corresponding to the maximum duration between these time markers, calculating a peak position value (PP) equal to the division of the difference between the instant associated with the maximum impedance value and the first instant which corresponds to the low impedance value, and the low duration, and optionally a rotation value (WR) equal to the division of the high duration by the low duration, determining the statistical distribution of the pulse data sets according to low duration/peak position value (PP) pairs or rotation value/peak position value (WR) pairs the statistics being established with respect to a set of ranges of values of pairs (Box 1, Box 2, Box 3, Box 4, Box 5, Box 6, Box 7, Box 8, Box 1', Box 2', Box 3', Box 4', Box 5',Box 6'), and classifying the blood sample by comparing the distribution of the the determined statistical distribution of the pulse data sets to a reference distribution of a sample of healthy blood.

* * * * *